United States Patent [19]

Yuspa et al.

[11] Patent Number: 4,722,895
[45] Date of Patent: Feb. 2, 1988

[54] SYNTHETIC PEPTIDES FOR THE PRODUCTION OF SPECIFIC KERATIN PROTEIN ANTIBODIES

[75] Inventors: Stuart H. Yuspa, Bethesda; Dennis R. Roop, Garrett Park; Peter M. Steinert, Rockville, all of Md.

[73] Assignee: The United States of America as represented by the Secretary, Dept. of Health & Human Services, Washington, D.C.

[21] Appl. No.: 654,213

[22] Filed: Sep. 25, 1984

[51] Int. Cl.$^4$ .................. C12P 21/00; C12P 21/02; C12N 15/00; C12Q 1/00
[52] U.S. Cl. ........................... 435/68; 435/70; 435/172.3; 435/7; 935/12
[58] Field of Search ............. 435/68, 70, 172.3, 6, 435/7; 935/12

[56] References Cited

U.S. PATENT DOCUMENTS 4,366,246 12/1982 Riggs et al. .................. 435/68

OTHER PUBLICATIONS

Roop et al., Proc. Nat'l. Acad. Sci. (USA) 80(3): 716–720, 1983.
Roop et al., J. Biol. Chem. 259 (13): 8037–8040, 1984.
Goodman et al., in *Methods in Enzymology*, vol. 68: 75–90, 1979.
Roop et al., *PNAS*, vol. 80, p. 716 (Feb. 1983).
Steinert et al., *Nature*, vol. 302, p. 794 (Apr. 1983).
Steinert et al., *Biochim. Biophys. Acta*, vol. 577, p. 11 (1979).

Primary Examiner—Thomas G. Wiseman
Assistant Examiner—Thomas D. Mays
Attorney, Agent, or Firm—John S. Roberts, Jr.

[57] ABSTRACT

A process is disclosed for the construction of synthetic peptides corresponding to amino acid sequences of 55-, 59-, 60-, 67-kilodalton keratin proteins. These synthetic peptides make possible the development of monospecific antisera for individual keratin proteins. The process involves preparing cDNA libraries and reducing the amino sequences of cDNA clones.

16 Claims, 3 Drawing Figures

```
67 kd    T V K F V S T S Y S R G T K-COOH
59 kd    T S G G G D Q S S K G P R Y-COOH
60 kd    K Y T T T S S S K K S Y R Q-COOH
50 kd    K V V S T H E Q V L R T K N-COOH
```

```
67 kd    T V K F V S T S Y S R G T K-COOH
59 kd    T S G G G D Q S S K G P R Y-COOH
60 kd    K Y T T T S S S K K S Y R Q-COOH
50 kd    K V V S T H E Q V L R T K N-COOH
```

SYNTHETIC PEPTIDES FOR THE PRODUCTION OF SPECIFIC KERATIN PROTEIN ANTIBODIES

BACKGROUND

Human cells contain a proteinaceous structural framework called a cytoskeleton. Each cell type contains a different protein or proteins as its cytoskeleton. For example, a brain cell's cytoskeleton is different than a muscle cell's or a lung cell's. In short, one means of differentiating cells is through an analysis of the proteins of the cytoskeleton.

Such differentiation, however, was only a theoretical concept due to the difficulty of differentiating epithelial cells. Epithelial cells form the epidermis and line hollow organs and all passages of the respiratory, digestive, and genito-urinary systems. Therein, however, lies the problem. It was discovered that epithelial cells could be distinguished from the other major cell types (mesenchymal, glial, neuronal, and muscle cells) by the presence of keratin proteins in the cytoskeleton.

The intermediate filaments found in keratinocytes and other epithelial cells are composed of about 20 different keratin subunits. Many of these subunits have common structural features. The subunits expressed in a given epithelial cell vary widely depending on cell type, period of embryonic development, degree of differentiation, and growth environment of the cell. Changes in the pattern of keratin synthesis have also been observed during experimental skin carcinogenesis, in established cell lines of malignant keratinocytes and in a variety of pathologic processes in the skin. Development of antisera specific to any one keratin subunit is, therefore, very useful for studies concerning expression and function of individual keratin proteins. This has proved difficult, however, since both polyclonal antibodies prepared against purified keratin subunits and monoclonal antibodies recognize more than one subunit. This shows that these antibodies are elicited against structural features common among keratin subunits. It is this similarity between the various keratin proteins that has made distinguishing between epithelial cells most difficult.

The first tests developed to differentiate between keratin subunits for the purpose of identifying specific epithelial cells involve monoclonal antibodies. These antibodies differentiate epithelial cells from non-epithelial cells, but they exhibit only limited utility in differentiating between specific epithelial cells—monoclonal antibodies have been developed that are specific for *groups* of keratin proteins.

The difficulty in developing highly specific monoclonal antibodies or a differentiating reagent lies in the inability to determine the exact amino acid sequence of the protein. Antibodies developed prior to this invention are specific for amino acid sequences of the keratin protein common to all of the keratins or groups of the keratins and are, therefore, not individually specific.

The present invention discloses a method for producing monospecific antibodies to the individual keratin proteins. The reagents of this invention, therefore, are useful as diagnositc and differentiation reagents. More importantly, perhaps, these antibodies are useful in detecting and identifying specific types of carcinomas, mesotheliomas, adenocarcinomas, and other forms of keratin-containing cancers. These antibodies are also useful in identifying the cellular source or origin of metastases of the aforementioned cancers.

The present invention was made possible by the discovery of two facets of the keratin protein: (1) cloning the gene for the keratin protein; and (2) establishing the amino acid sequences for the cloned keratin gene. The combination of these discoveries led to the elucidation of the amino acid sequences for the keratin protein. In broad terms, the invention is the development of antibodies specific for amino acid sequences particular to each keratin protein. Disclosed is the method for producing antibodies specific for keratins of 55, 59, 60, and 67 molecular weight.

Utility

The process of this invention is useful in the histodiagnosis and classification of tumors and for the identification of transformed cells which contain keratin.

GENERAL DESCRIPTION

Figures 1, 2:
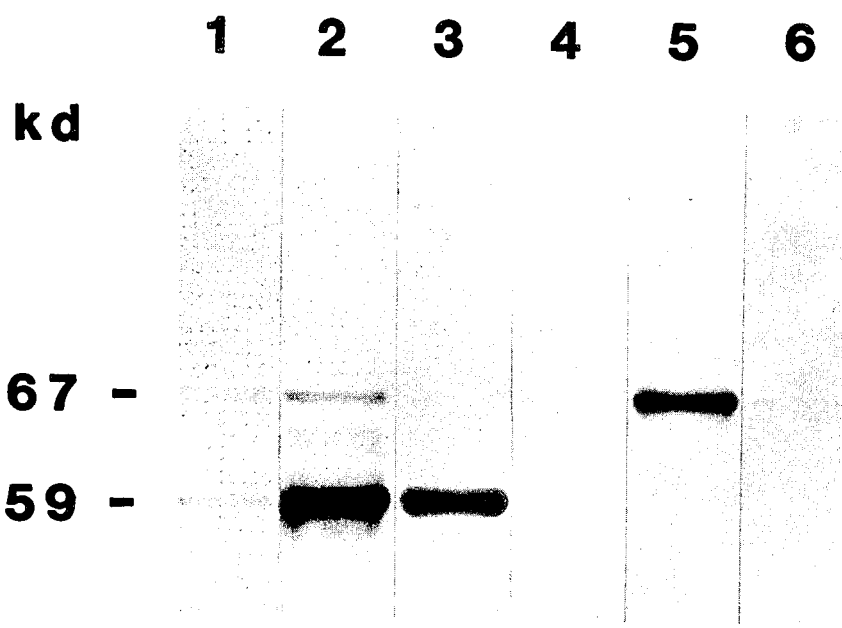
FIG. 1 is a comparison of amino acid sequences at the carboxy terminus of mouse keratins. Amino acid sequences were deduced from the nucleotide sequence of cDNA clones. Regions of the 67 and 59 kd keratins selected for synthesis are underlined.
FIG. 2 is an immunoblot analysis of antisera. A cytoskeletal extract of newborn mouse epidermis was subjected to electrophoresis, transferred to nitrocellulose paper and reacted with different antisera. Lane 1 was stained directly with Coomassie Blue. Lanes 2-6 were reacted with the following antisera: 2, a multivalent keratin antiserum (1/25,000 dilution); 3, anti-59 kd keratin peptide (1/2,000 dilution); 4, preimmune serum for the anti-59 kd keratin peptide (1/2,000 dilution); 5, anti-67 kd keratin peptide (1/800 dilution); and 6, preimmune serum for the anti-67 kd keratin peptide (1/800 dilution).

Synthetic peptides corresponding to the carboxy terminal amino acid sequences of mouse keratins are used to produce antibodies which are highly specific for subunits unique to each keratin protein.

cDNA libraries to mRNA isolated from both terminally differentiating murine epidermis and undifferentiated murine epidermal cells (basal cells) are prepared. The cloned gene to the 59 and 67 Kd keratins expressed in the former and 50 and 60 Kd keratins expressed in basal cells are sequenced to deduce their amino acid sequence.

Once the amino acid sequence of the gene is determined, the amino acid sequence of the keratin protein can be determined. Once the protein is sequenced, synthetic peptides corresponding to the unique amino acid sequence (the carboxy terminal amino acid sequences) are produced. These peptides are then used as immunogens which elicit highly specific keratin antibodies. In short, the procedure involves cloning the gene for a specific keratin protein, sequencing that gene, determining the amino acid sequences of the protein corresponding to the gene, producing synthetic peptides corresponding to the protein, and producing antibodies elicited by using the peptides as an immunogen. Other facets of the invention are disclosed in the Specific Disclosure.

Specific Disclosure

A library of cDNA clones is prepared from poly(A)+ RNA of newborn mouse epidermis. An epidermis sample is placed in liquid nitrogen and ground in a mortar. RNA is isolated from the ground epidermis with guanidine.HCl and enriched for poly(A)+ RNA using the procedure described in Fuchs and Green, *Cell*, Vol. 17, pp 573–582 (1979). 150 µg of epidermal poly(A)+ RNA obtained after the enrichment process is separated by electrophoresis in a 1.5% agarose gel containing 10 mM methylmercuryhydroxide. The gel is sliced into 2-mm fractions and the RNA isolated as described by Fuchs and Green, above. This RNA is then used to construct a cDNA library.

Double-stranded cDNA is synthesized with reverse transcriptase from poly(A)+ RNA isolated, above, and the hairpin loop is cleaved with S1 nuclease. Approximately 16 dCMP residues are added to the 3' ends of the double-stranded cDNA with terminal transferase. The tailed cDNA is annealed with plasmid vector pBR322 that had been linearized by cleavage with PstI restriction endonuclease and tailed with an average of 14 dGMP residues per 3' terminus. An aliquot of this mixture was used to transform *Escherichia coli* K-12 strain RRI. Transformants containing recombinant plasmids with keratin cDNA inserts are identified by colony hybridization with [$^{32}$P]cDNA complementary to partially purified keratin mRNAs.

Recombinant plasmids produced above are then shown by hybrid selection analysis to contain cDNA sequences complementary to the mRNA encoding the 55 Kd, 59 Kd, 60 Kd, and 67 Kd keratins.

The next step is determining the nucleotide sequences of these clones. Sequencing is carried out following 5' and 3' labelling of appropriate fragments on both strands using the Maxam and Gilbert procedures in *Meth. Enzym.*, Vol. 65, pp 499–560 (1980). The clone pK 276 (0.536 kbp) began just upstream from the first NciI site and pK 435 (1.802 kbp) began two bases upstream from a DdeI site. Both clones are used as examples and encode the 59 Kd keratin. The 5'-terminal sequence is then derived following primer extension of a probe consisting of a DdeI-SacI fragment.

Once the nucleotide sequencing is performed, the amino acid sequence of the protein is deduced based on the codons elucidated by the nucleotide sequencing. The carboxy terminal amino acid sequences for each keratin is shown in FIG. 1.

Synthetic peptides are then synthesized corresponding to the sequences shown in FIG. 1. Decatripeptides and decadipeptides are synthesized by well-known solid-phase methods and are purified by high performance liquid chromatography. See Meyers and Coy, *Int. J. Peptide Protein Res.*, Vol. 16, pp 248–253 (1980) for a review.

The preferred peptides of the present invention are VKFVSTSYSRGTK, GGGDQSSKGPRY, KYTTTSSSKKSYRQ, and KVVSTHEQVLRTKN.

Each individual letter represents a different amino acid, as follows:

| | | | |
|---|---|---|---|
| arginine | R | asparagine | N |
| aspartic acid | D | glutamine | Q |
| glutamic acid | E | glycine | G |
| histidine | H | leucine | L |
| lysine | K | phenylalanine | F |
| proline | P | serine | S |
| threonine | T | tyrosine | Y |
| valine | V | | |

These synthetic peptides are then coupled to bovine serum albumin (following the procedure described in Walter et al, *PNAS*, Vol. 77, pp 5197–5200 (1980)) and used to immunize rabbits according to the following schedule:

(1) 500 µg of coupled peptide in complete Freund's adjuvant (1:1) subcutaneously on day 0, (2) 500 µg of coupled peptide in incomplete Freund's adjuvant (1:1) subcutaneously on day 21, (3) 500 µg of coupled peptide in incomplete Freund's adjuvant (1:1) subcutaneously on day 42.

Blood taken from these animals after 7 weeks was shown by ELISA analysis to contain highly specific antibodies corresponding to synthetic peptides for keratins of m.w. 55, 59, 60, and 67. The specificity of the antisera is determined by immunoblot analysis against a cytoskeletal extract of newborn mouse epidermis, which mainly consists of the 59 and 67 kd keratins (FIG. 2, lane 1).

A previously described multivalent keratin antiserum, which was prepared against a partially purified preparation of the 59 kd keratin subunit, reacts with both the 67 and 59 kd keratins as well as with minor polypeptides of 64 and 62 kd. Both antisera produced against synthetic peptides are highly specific for their corresponding keratin polypeptide (FIG. 2, lane 3 and 5). Weak activity against the 67 kd keratin is present in both preimmune sera (FIG. 2 lanes 4 and 6) and is also observed in the anti-59 kd keratin peptide antiserum (FIG. 2, lane 3).

EXAMPLE 1

Cloning of Keratin cDNAs. Double stranded cDNA was synthesized with reverse transcriptase from poly(A))+ RNA isolated from newborn mouse epidermis and the hairpin loop was cleaved with S1 nuclease. Approximately 16 dCMP residues were added to the 3' ends of the double-stranded cDNA with terminal transferase. The tailed cDNA was annealed with plasmid vector pBR322 that had been linearized by cleavage with PstI restriction endonuclease and tailed with an average of 14 dGMP residues per 3' terminus. An aliquot of this mixture was used to transform *Escherichia coli* K-12 strain RRI. Transformants containing recombinant plasmids with keratin cDNA inserts were identified by colony hybridization with [$^{32}$P]cDNA complementary to partially purified keratin mRNAs. Plasmid DNA was then prepared from positive recombinants.

EXAMPLE 2

Hybridization-Selection Assay. The identity of recombinants selected in the initial screening was confirmed by the hybrid-selection assay essentially as described by Cleveland et al, *Cell*, Vol. 20, pp 95–109 (1980). Plasmid DNAs were linearized with EcoRI and 10 µg was bound to (13-mm) nitrocellulose filters (Schleicher and Schuell, BA85). The filter-bound DNA was prehybridized for 2 hr at 41° C. in 50% (vol/vol) formamide (Fluka)/0.4 M NaCl/10 mM 1,4-piperazine-diethanesulfonic acid, pH 6.4/5 mM EDTA/250 μg of poly(A)+ per ml/250 μg of yeast tRNA per ml/0.2% NaDodSO4. Hybridization was for 20 hr at 41° C. in the same buffer (150 μl per filter) containing 15 μg of epidermal poly(A)+ RNA. The filters were washed two times (5 min each) with 1×NaCl/Cit/0.1% NaDodSO4 at room temperature [1×NaCl/Cit is 0.15 M NaCl/0.015 M trisodium citrate (standard saline citrate)], three times (5 min each) with 0.1×NaCl/Cit/0.1% NaDodSO4 at room temperature, and two times (5 min each) with 0.1×NaCl/Cit/0.1% NaDodSO4 at 60° C. for filters containing pK335 and pK1005 DNA and at 68° C. for the filter containing pK276 DNA. RNA was eluted from the filters in 300 μl of water at 100° C. for 2 min. The RNA was collected by precipitation in the presence of 10 μg of yeast tRNA and analyzed by translation in the rabbit reticulocyte system.

EXAMPLE 3

Figure 3:
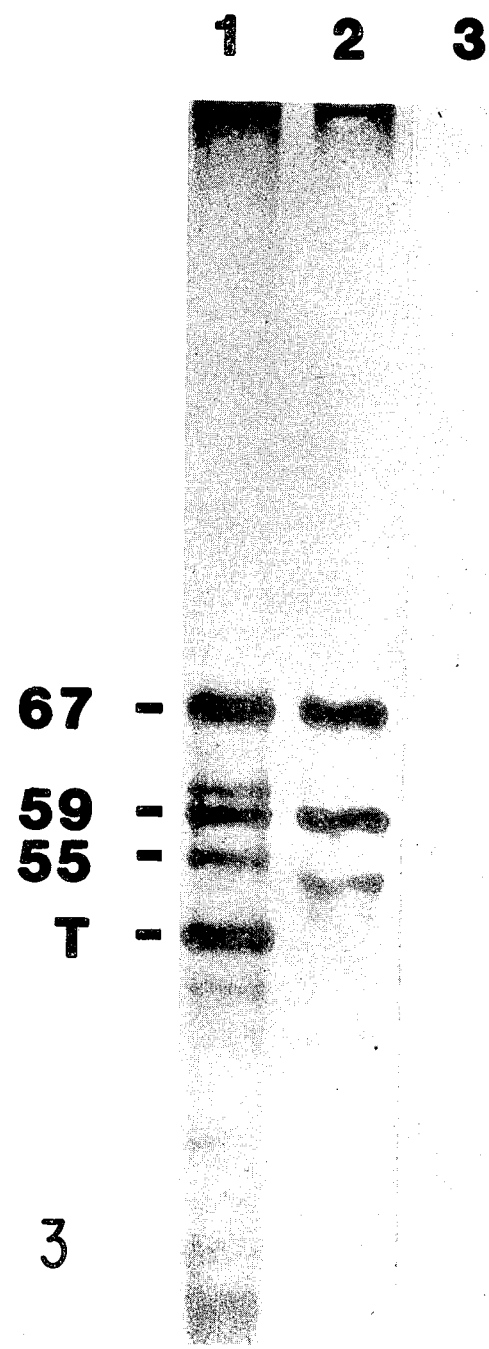
FIG. 3 shows translation products of mouse epidermal poly(A)+ RNA. (Poly(A)+ RNA was extracted from newborn mouse epidermis and translated in an in vitro reticulocyte system containing [$^{35}$S]-methionine. The labeled proteins were separated electrophoretically in an 8.5% polyacrylamide/NaDodSO$_4$ gel and visualized by fluorography. Lane 1, translation products of mouse epidermal poly(A)+ RNA. Lane 2, translation products immunoprecipitated with keratin antiserum. Lane 3, translation products that had been allowed to react with control serum. The 55-kDal band is distorted by unlabeled IgG in the immunoprecipitate. T indicates an mRNA-independent artifact of the translation system.

Cloning DNAs Complementary to Keratin mRNAs. The translation products of total poly(A)+ RNA isolated from newborn mouse epidermis are shown in FIG. 3, lane 1. Immunoprecipitation of these products with antiserum prepared against keratins present in mouse stratum corneum demonstrated that the most abundant mRNAs present in this tissue encode for keratins that are 55, 59, and 67 Kdal (FIG. 3, lane 2). Previous studies have shown that this multivalent rabbit antiserum is able to react with most, if not all, of the keratins synthesized in intact epidermis and cultured epidermal cells. The band below T in lane 1 is actin. Because the concentration of keratin mRNAs was quite high in mouse epidermis, a cDNA library was constructed with cDNA synthesized from total epidermal poly(A)+ RNA. Recombinant plasmids were screened with cDNA synthesized from partially purified mRNA coding for the 59- and 67-kDal keratins. These mRNAs were obtained by fractionating epidermal poly(A)+ RNA in a 1.5% agarose gel containing 10 mM methylmercury hydroxide. The gel was sliced into 2.0 mm fractions and the RNA was isolated from each slice. Fractions 11 and 14 were enriched in mRNA coding for the 67- and 59-kDal keratins and these were used for the synthesis of [$^{32}$P]cDNA. In the process of screening the cDNA library with these cDNAs, recombinants that contained sequences complementary to the mRNA coding for the 55-kDal keratin were also isolated.

We claim:

1. A process for producing antibodies specific for one specific keratin protein consisting essentially of
   isolating mRNA from murine epidermis cells;
   preparing cDNA clones for said mRNA;
   ligating said cDNA to a host plasmid vector to form a recombinant plasmid;
   transforming E. coli with said recombinant plasmid in order to produce cDNA;
   sequencing said cDNA, deducing amino acid sequences of protein and selecting unique amino acid portion which characterizes a single keratin;
   synthesizing the unique amino acid sequence using an amino acid synthesizer in order to produce synthetic peptides;
   immunizing rabbits with said synthetic peptides in order to produce antibodies specific for individual keratin proteins; and
   isolating siad antibodies and testing specificity by immunofluorescent and immunobloting techniques.

2. The process of claim 1 wherein said cDNA encodes a peptide having an amino acid sequence unique to a 59 Kd keratin.

3. The process of claim 1 wherein said cDNA encodes a peptide having an amino acid sequence unique to a 67 Kd keratin.

4. The process of claim 1 wherein said cDNA encodes a peptide having an amino acid sequence unique to a 60 Kd keratin.

5. The process of claim 1 wherein said cDNA encodes a peptide having an amino acid sequence unique to a 55 Kd keratin.

6. The process of claim 1 wherein said cDNA clones are prepared from mRNA by adding reverse transcriptase to poly(A) RNA;
   cleaving said poly(A) RNA with S1 nuclease to form double-stranded cDNA;
   adding terminal transferase to said doublestranded cDNA to form tailed cDNA; and
   annealing said tailed cDNA to a plasmid vector replicable in E. coli.

7. The process of claim 1 wherein said host plasmid vector is pBR322.

8. The process of claim 1 wherein synthetic peptides are formed containing the following amino acid sequences:

V K F V S T S Y S R G T K

9. The process of claim 1 wherein synthetic peptides are formed containing the following amino acid sequences:

G G G D Q S S K G P R Y

10. The process of claim 1 wherein synthetic peptides are formed containing the following amino acid sequences:

K Y T T T S S S K K S Y R Q

11. The process of claim 1 wherein synthetic peptides are formed containing the following amino acid sequences:

K V V S T H E Q V L R T K N

12. The process of claim 1 wherein antibodies produced react with specificity to 59 Kd keratin.

13. The process of claim 1 wherein antibodies produced react with specificity to a 67 Kd keratin.

14. The process of claim 1 wherein antibodies produced react with specificity to a 55 Kd keratin.

15. The process of claim 1 wherein antibodies produced react with specificity to a 60 Kd keratin.

16. A process for the production of synthetic keratin peptides comprising
    forming a recombinant plasmid containing cDNA corresponding to a keratin protein;
    transforming E. coli with said recombinant plasmid in order to produce cDNA;
    analyzing said cDNA to determine its cDNA amino acid sequences;
    deducing the amino acid sequence of said keratin protein from said cDNA amino acid sequences;
    selecting a unique portion of said amino acid sequence corresponding to an individual keratin protein; and
    synthesizing synthetic peptides corresponding to said unique portion using an amino acid synthesizer.

* * * * *

UNITED STATES PATENT AND TRADEMARK OFFICE
CERTIFICATE OF CORRECTION

PATENT NO. : 4,722,895

DATED : February 2, 1988

INVENTOR(S) : Yuspa et al.

It is certified that error appears in the above-identified patent and that said Letters Patent is hereby corrected as shown below:

Please amend claim 1 to read:
--A process for producing antibodies specific for one specific keratin protein consisting essentially of isolating mRNA from murine epidermis cells;
  preparing cDNA from said mRNA:
  cloning said cDNA by ligating said cDNA to a plasmid DNA vector to form a recombinant plasmid;
  transforming E. coli with said recombinant plasmid in order to replicate the cloned DNA;
  sequencing said cloned DNA, deducing predicted amino acid sequences of protein encoded by said cloned DNA and selecting amino acid portion which is unique for a single keratin;
  synthesizing the unique amino acid sequence using an amino acid synthesizer in order to produce synthetic peptides;
  immunizing rabbits with said synthetic peptides in order to produce antibodies specific for individual keratin proteins;
  isolating said antibodies;
and testing the specificity of said antibodies for said unique amino acid sequence --

Signed and Sealed this

Thirtieth Day of August, 1988

Attest:

DONALD J. QUIGG

Attesting Officer

Commissioner of Patents and Trademarks